(12) United States Patent
Giordano et al.

(10) Patent No.: US 6,596,698 B1
(45) Date of Patent: Jul. 22, 2003

(54) METHODS OF INHIBITING SMOOTH MUSCLE CELL PROLIFERATION AND PREVENTING RESTENOSIS WITH A VECTOR EXPRESSING RB2/P130

(75) Inventors: Antonio Giordano, Philadelphia, PA (US); Pier P. Claudio, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/787,020

(22) PCT Filed: Sep. 10, 1999

(86) PCT No.: PCT/US99/20723
§ 371 (c)(1),
(2), (4) Date: May 2, 2001

(87) PCT Pub. No.: WO00/15649
PCT Pub. Date: Mar. 23, 2000

Related U.S. Application Data (60) Provisional application No. 60/099,896, filed on Sep. 11, 1998.

(51) Int. Cl.$^7$ .......................... A61K 31/70; A61K 48/00; C12N 15/74; C12N 5/02; C12N 15/09

(52) U.S. Cl. ...................... 514/44; 435/320.1; 435/325; 435/455; 424/93.2; 424/93.21

(58) Field of Search ........................... 514/44; 424/93.2, 424/93.21; 435/455, 320.1, 325

(56) References Cited

PUBLICATIONS

Reilly et al., Pharmacological and mechanistic aspects concerning the use heparin and Beta–cyclodextrin tetradecasulfate for the treatment of vascular restenosis, 1993, Drug Development Research, vol. 29, pp. 137–147.*
Johnson et al., The utility of animal models in the preclinical study of interventions to prevent human coronary artery restenosis: Analysis and recommendations, 1999, Thromb, Haemost., vol. 81, pp. 835–843.*
Muller et al., Experimental models of coronary artery restenosis, 1992, JACC, vol. 19, pp. 418–432.*
Lafont et al., Why do animal models of post–angioplasty restenosis sometimes poorly predict the outcome of clinical trials?, 1998, Card. Res., vol. 39, pp. 50–59.*
Miller et al., Targeted vectors for gene therapy, 1995, FASEB, vol. 9, pp. 190–199.*
Deonarain, Ligand–targeted receptor–mediated vectors for gene delivery, 1998, Exp. Opin. Ther. Patents, vol. 8, pp. 53–69.*
Eck et al., Gene–based therapy, 1995, Pharmacological Basis of Therapeutics, pp. 77–101.*

Chang, M.W. et al., "Cytostatic Gene Therapy for Vascular Proliferative Disorders with a Constitutively active form of the Retinoblastoma Gene Product", Science, (1995), vol. 267, pp 518–522.
De Luca et al., "The Retinoblastoma Gene Family and its Role in Proliferation, Differentiation and Development", Histol. Histopatho. (1996), vol. 11(4), pp 1029–1034.
Claudio P.P. et al., "P130/PRB2 has Growth Suppressive Properties similar to yet Distinctive from those of Retnioblastoma Family Members PRB and P107", Cancer Research, (1994), vol. 54, No. 21, pp 5556–5560.
Baldi et al. (1995) The Rb2/p130 Gene Product is a Nuclear Protein Whose Phosphorylation is Cell Cycle Regulated, Journal of Cellular Biochemistry, 59:402–408.
Drechsel et al. (1998) Mechanismen und Pravention der Restenose nack Koronar–angioplastie, Schweiz Med Wochenaschr, 128:497–507 (Abstract in English).
Feldman et al. (1995) Prevention of restenosis after coronary angioplasty: towards a molecular approach?, Fundam Clin Pharmacol, 9:8–16.
Feldman et al. (1996) Perspectives of arterial gene therapy for the prevention of restenosis, Cardiovascular Research, 32:194–207.
Howard et al. (1998) Retinoblastoma–Related Protein pRb2/p130 and Suppression of Tumor Growth In Vivo., J Natl Cancer Inst. 90:1451–1460.
Radar DJ (1997) Gene therapy for atherosclerosis, Int J Clin Lab Res, 27:35–43.
Wickham et al., "Targeting adenovirus gene transfer to enothelial and smooth muscle cells by using bispecific antibodies" Journal of Virology, 1996, vol. 70, No. 10, pp. 6831–6838.
Feldman al., "Prevention of restenosis after coronary angioplasty: Towards a Molecular approach", Fundamental and Clinical Pharmacology, 1995, vol. 9, No. 1, pp. 8–16.
Feldman, et al., "Perspectives of arterial gene therapy for the prevention of restenosis", Cardiovascular Research, 1996, vol. 32, No. 2, pp. 194–207.
Radar, D.J., "Gene Therapy for atherosclerosis", International Journal of Clinical and Laboratory Research, 1997, vol. 27, No. 1, pp. 34–43.
Baldi et al., "The Rb2/p130 gene product is a nuclear protein whose phosphorylation is cell cycle regulated", Journal of Cellular Biochemistry, 1995, vol. 59, No. 3, pp. 402–208.
Howard et al., "Retinoblastoma–related protein pRb2/p130 and suppression of tumor growth in vivo", Journal of National Cancer Institute, Oct. 7, 1998, vol. 90, No. 19, pp. 1451–1460.

* cited by examiner

Primary Examiner—Anne M. Wehbe'
Assistant Examiner—Q. Janice Li
(74) Attorney, Agent, or Firm—ReedSmith LLP; William J. McNichol, Jr.; Nanda P. B. A Kumar (57) ABSTRACT

Methods of inhibiting vascular smooth muscle cell proliferation and preventing restenosis by transducing the vascular smooth muscle cells with a viral veactor expressing RB2/p130 are provided.

2 Claims, 11 Drawing Sheets

CELL CYCLE DATA

Mean G1 = 90.8
CV G1 = 5.9
% G1 = 53.7

Mean G2 = 179.0
CV G2 = 10.3
% G2 = 18.5

% S = 27.8

G2/G1 = 1.970

% B.D. = 1.0
Chi Sq. = 3.6

Fig. 2A

CELL CYCLE
DATA

Mean G1 = 96.8
CV G1 = 5.2
% G1 = 57.1

Mean G2 = 189.9
CV G2 = 7.9
% G2 = 15.9

% S = 27.0

G2/G1 = 1.961

% B.D. = 1.3
Chi Sq. = 2.2

Fig. 2B

CELL CYCLE DATA

Mean G1 = 86.3
CV G1 = 4.5
% G1 = 87.5

Mean G2 = 170.5
CV G2 = 4.6
% G2 = 6.1

% S = 6.4

G2/G1 = 1.976

% B.D. = 0.7
Chi Sq. = 2.7

Ad-CMV  Ad-Rb2/p130

Control 1

Control 2

METHODS OF INHIBITING SMOOTH MUSCLE CELL PROLIFERATION AND PREVENTING RESTENOSIS WITH A VECTOR EXPRESSING RB2/P130

This application is the United States national stage of International Application No. PCT/US99/20723, filed Sep. 10, 1999, which was published under PCT Article 21 (2) in English as International Publication No. WO 00/15649, and which claims benefit of priority of U.S. Provisional Application No. 60/099,896 filed Sep. 11, 1998, now abandoned.

INTRODUCTION

This invention was made in the course of research sponsored by the National Institutes of Health. The U.S. Government may have certain rights in this invention.

BACKGROUND OF THE INVENTION

Cardiovascular disease is the leading cause of mortality in the western world (Ross, R. Nature 362, 801–809 (1993); Landau et al. N. Engl. J. Med. 330, 981–993 (1994)) In the United States and other industrialized countries ischemic heart disease, resulting in angina pectoris, myocardial infarction (MI), and sudden death, prevails as the principal cause of death and comprises at least 80% of all deaths from heart disease (Braunwald, E. In Heart disease: a textbook of cardiovascular medicine. Saunders W. B. Ed., (1996)) The vast majority of cases of ischemic heart disease are a consequence of atherosclerosis of the coronary arteries (Ross, R Nature 362, 801–809 (1993)). The treatment of occlusive coronary artery disease (CAD) involves three approaches, used individually or in combination: 1) coronary artery by-pass grafting (CABG); 2) percutaneous transluminal coronary angioplasty (PTCA), with or without stent application; and/or 3) medical management. While PTCA is less invasive and more cost effective than CABG, it bears some limitations. One disadvantage of PTCA is that restenosis of the artery occurs in as many as 30 to 50% of cases within 3 to 6 months of the procedure (Landau et al. N. Engl. J. Med. 330,981–993 (1994); Braunwald, E. In Heart disease: a textbook of cardiovascular medicine. Saunders W. B. Ed., (1996); Serruys et al. Circulation. 77,361–71 (1988); Holmes et al. Am. J. Cardiol. 53, 77C–81C (1984); Guiteras et al. Am. J. Cardiol. 60, 50B–55B (1987)) . A variation of this technique is stent application in the dilated artery segment. Following promising preliminary reports, further investigation demonstrated that in the long-term the percentage of restenosis following stent-PTCA is similar to that of PTCA alone. In fact, in-stent restenosis is a frequent complication of stent-PTCA (Belli, G., Ellis, S. G., Topol, E. J. Stenting for ischemic heart disease. In "progress in cardiovascular diseases" W. B. Sunders Ed. pp 159–182 (1997)). No effective treatment for hindering restenosis is currently available. It is well documented that chronic or acute injury (such as from PTCA) to the arterial wall induces the expression of a variety of growth factors and inflammatory cytokines that stimulate smooth muscle cell (SMC) proliferation and migration from the media into the intirna resulting in neointima formation and eventual restenosis (Clowes et al. Lab. Invest. 49, 208–215 (1983)). Inhibition of neointima formation should greatly improve the effectiveness of PTCA in the long term management of CAD. Numerous growth factors induce SMC proliferation through a variety of signal transduction pathways in vitro and in vivo (Libby et al. Circulation 86 (Suppl III) 47–52 (1992)). Accordingly, several regulatory proteins of the cell cycle machinery, instead of the upstream signal transduction molecules, have been suggested as targets for effective cytostatic therapy of vascular proliferative disorders. For example, Morishita et al. disclose studies wherein single intraluminal delivery of antisense cdc2 kinase and proliferating-cell nuclear antigen oligonucleotides resulted in chronic inhibition of neointimal hyperplasia. Proc. Acad. Natl. Sci. 90, 8474–8478 (1993). Chang et al. disclose results from studies suggested to demonstrate the role of (retinoblastoma) Rb in regulating vascular smooth muscle cell proliferation and to suggest a gene therapy approach for vascular proliferation disorders associated with arterial injury. Science. 267, 518–522 (1995). Smith et al. also analyzed the effects of full-length phosphorylation competent and mutant truncated forms of human Rb for their effects on vascular smooth muscle proliferation and neointima formation. Circulation 1997 96(6) 1717–9. These analyses are taught to reveal that the maintenance of high levels of phosphorylation competent human Rb either full-length or truncated forms in vascular smooth muscle cells is an effective method of modulating the extent of intimal hyperplasia that occurs after balloon induced vascular injury. Smith et al. Circulation. 96, 1899–1905 (1997)).

Another member of the retinoblastoma family, RB2/p130, has also been shown to have a regulatory role in cell cycle function. Baldi et al. have shown that phosphorylation of the RB2/p130 gene product is regulated in a cell cycle dependent manner (Baldi et al. J. Cell. Biochem. 59:402–408 (1995)), in the same way that the phosphorylation of Rb is cell cycle dependent (DeCaprio et al. Cell 58:1085–1095 (1989)). Further, the growth suppressive properties of the gene product of RB2/p130 have been shown to be specific for the $G_1$ phase in similar fashion to pRb and pl07 (Claudio et al. Cancer Res. 56:2003–2008 (1996)). The gene product of RB2/p130 has also been shown to arrest growth in human tumor cell lines in a manner similar to the other members of the Rb family (i.e., pRb and pl07). However, this protein also inhibits proliferation in a glioblastoma cell line that is resistant to the growth suppressive effects of both pRb and pl07 (Claudio et al. Cancer Res. 54:5556–5560 (1994)). Accordingly, RB2/p130 has similar yet distinctive growth suppressive properties from pRb and pl07 (Claudio et al., Cancer Res. 54:5556–5560 (1994)).

It has now been found that localized arterial transduction of RB2/p130 via a viral vector at the time of angioplasty drastically reduces neointimal hyperplasia and prevents restenosis. Furthermore, the ability of RB2/p130 to block proliferation correlates with its ability to bind and sequester the E2F family of transcription factors, which are important mediators of cell cycle progression. Accordingly, RB2/p130 is believed to be an important target for vascular gene therapy.

SUMMARY OF THE INVENTION

An object of the present invention is to provide a method of inhibiting vascular smooth muscle cell proliferation which comprises transducing vascular smooth muscle cells with a viral vector expressing RB2/p130.

Another object of the present invention is to provide a method of preventing restenosis in a patient which comprises administering to a patient a viral vector expressing RB2/p130.

DETAILED DESCRIPTION OF THE INVENTION

Smooth muscle cell (SMC) proliferation resulting in neointima formation is implicated in the pathogenesis of atherosclerotic plaques and accounts for the high rates of restenosis following percutaneous transluminal coronary angioplasty (PTCA) with or without stent application, a widespread treatment for coronary artery disease (CAD). Endothelial lesions trigger intense proliferative signals to the SMCs of the subintima, stimulating their re-entry into the cell cycle from a resting $G_0$ state, resulting in neointima formation and vascular occlusion. Cellular proliferation is negatively controlled by growth regulatory and/or tumor suppressor genes, such as the retinoblastoma (Rb) gene family members (RB/p105, p107, RB2/p130).

Accordingly, the retinoblastoma family proteins (pRb/p105, p107, and RB2/p130) are excellent candidates for vascular disease gene therapy. They are nuclear phosphoproteins with growth suppressive properties that interact with specific members of the E2F transcription factor family (E2F1-5) and are regulated by phosphorylation/dephosphorylation events in a cell cycle dependent manner (Weinberg, R. A. Cell 85, 457–459 (1996); and Nevins et al. J. Cell. Physiol. 173, 233–236 (1997)). Studies have shown that induction of RB2/p130 expression growth arrests proliferating cells in the $G_0/G_1$ phase of the cell cycle by directly interacting with and regulating the activity of the cell cycle machinery (Claudio et al. Cancer Research 54, 5556–5560 (1994); Claudio et al. Cancer Res. 56, 2003–2008 (1996); and De Luca et al. J. Biol. Chem. 272, 20971–20974 (1997)) Furthermore, induction of pRB2/p130 expression inhibits cellular proliferation in certain cell lines that are refractory to the effects of Rb family members pRb/p105 and p107 (Claudio et al. Cancer Research 54, 5556–5560 (1994); De Luca et al. J. Biol. Chem. 272, 20971–20974 (1997)). It has now been found that adenovirus-mediated transduction of RB2/p130 blocks SMC proliferation in vivo and in vitro. Moreover, it has now been shown that RB2/p130 preferentially interacts with and sequesters the growth promoting transcriptional activity of E2F4 in SMCs.

Adenoviruses have been shown to serve as effective and efficient vectors to deliver transgenes to cells in vivo. Accordingly, in these experiments, Adenoviral mediated-RB2/p130 gene transfer was used to hold in check the proliferative capacity of the arteriai smooth muscle subsequent to acute injury in order to prevent restenosis following angioplasty.

Figure 1A:
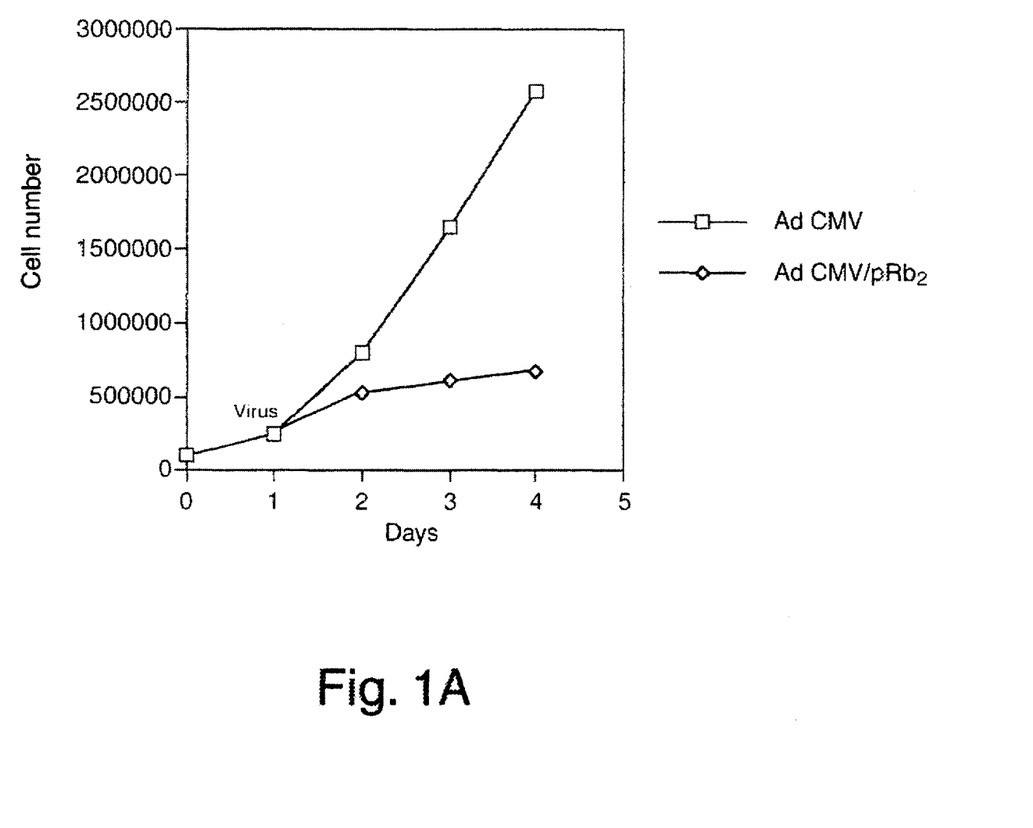
FIGS. 1a–1b show the effects of adenoviral transduction of the RB2/p130 gene on the growth of rat pulmonary artery smooth muscle cells (PASM) and Western blot demonstrating pRb2/p130 expression in PASM cells transduced with Ad-CMV (empty viral vector) or Ad-CMV-Rb2/p130 over time.
Figure 1B:
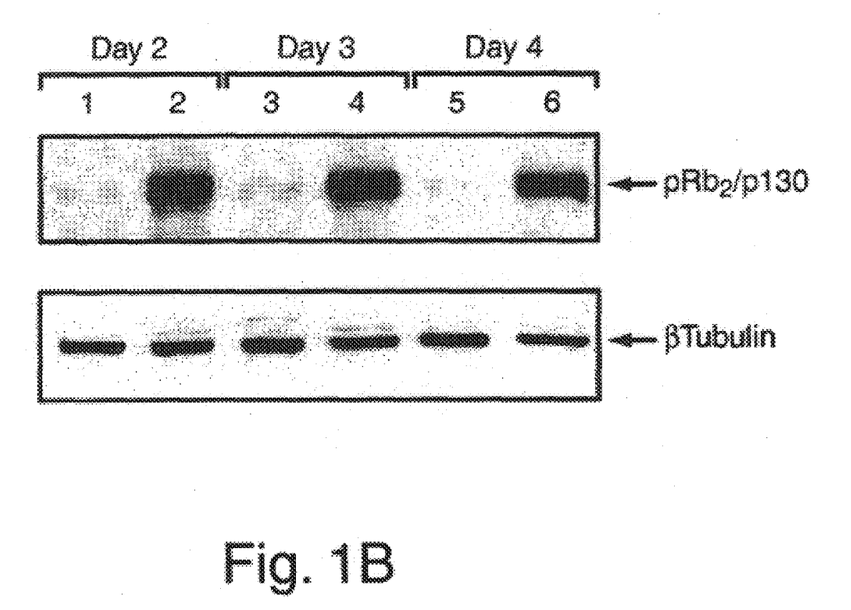

The effects of viral transduction of the RB2/p130 gene on the growth of a pulmonary artery smooth muscle cell line (PASM) was examined. The PASM cell line expresses many differentiation markers off SMCs and is therefore considered a good paradigm (Roberts et al. EMBO J. 15, 6301–6310 (1996); Rothman et al. Circulation. 86, 1977–1986 (1992)). In these experiments, PASM cells were plated at a density of $1 \times 10^5$ in 10 cm diameter dishes in triplicates and transduced with 50 pfu/cell of either Ad-CMV or Ad-CMV-RB2/p130. Cells were counted by trypan blue exclusion method each day over a week to monitor their growth rate. In PASM cells transduced with Ad-CMV-RB2/p130 the growth rate was inhibited by 5 fold as compared to that of Ad-CMV transduced cells.

To measure the expression level of RB2/p130 in Ad-CMV-RB2/p130 and Ad-CMV transduced cells, cells were harvested each day for one week and western blot analysis was performed on extracts. At each time point, the expression of RB2/p130 was ~200 fold higher in the Ad-CMV-RB2/p130 than in the Ad-CMV transduced cells. The blot was normalized for equal loading and transfer of proteins by blotting the membrane with anti-β Tubulin as well as staining the membrane with Coomassie brilliant blue.

Figure 2A:
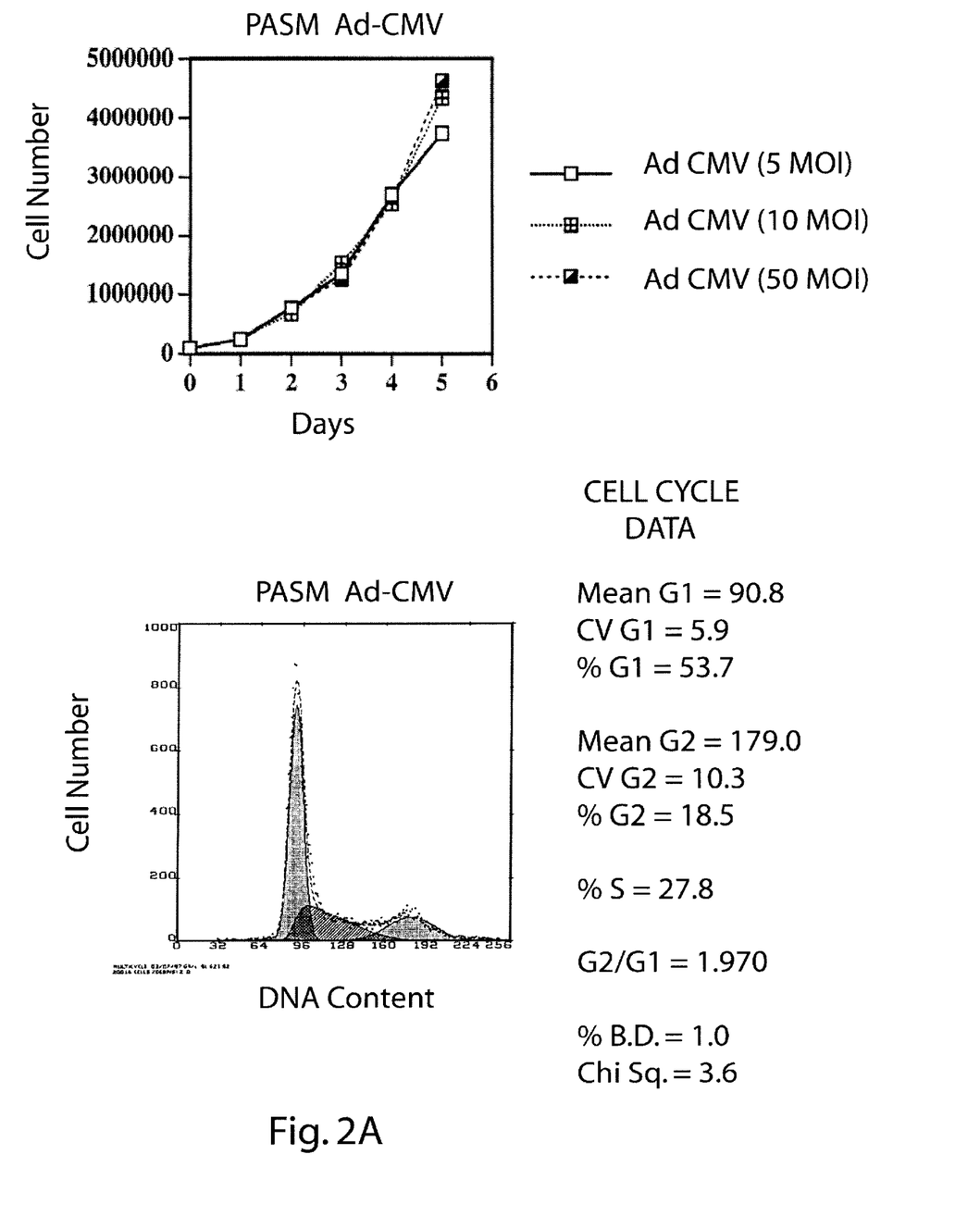
FIGS. 2a–2c show the effects of increasing quantities of Adenoviral particles on the growth of a pulmonary artery smooth muscle cell line (PASM).
Figure 2B:
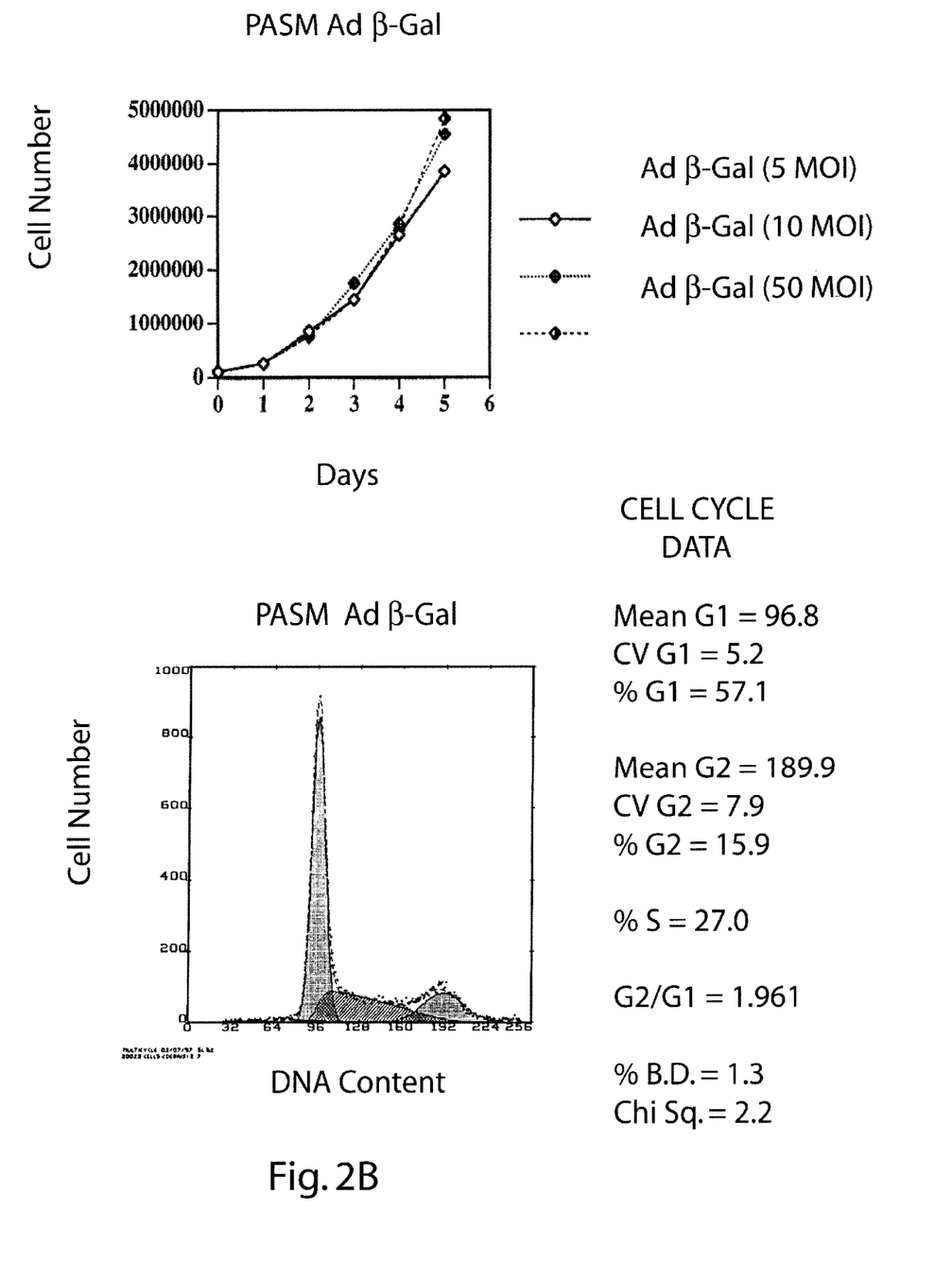
Figure 2C:
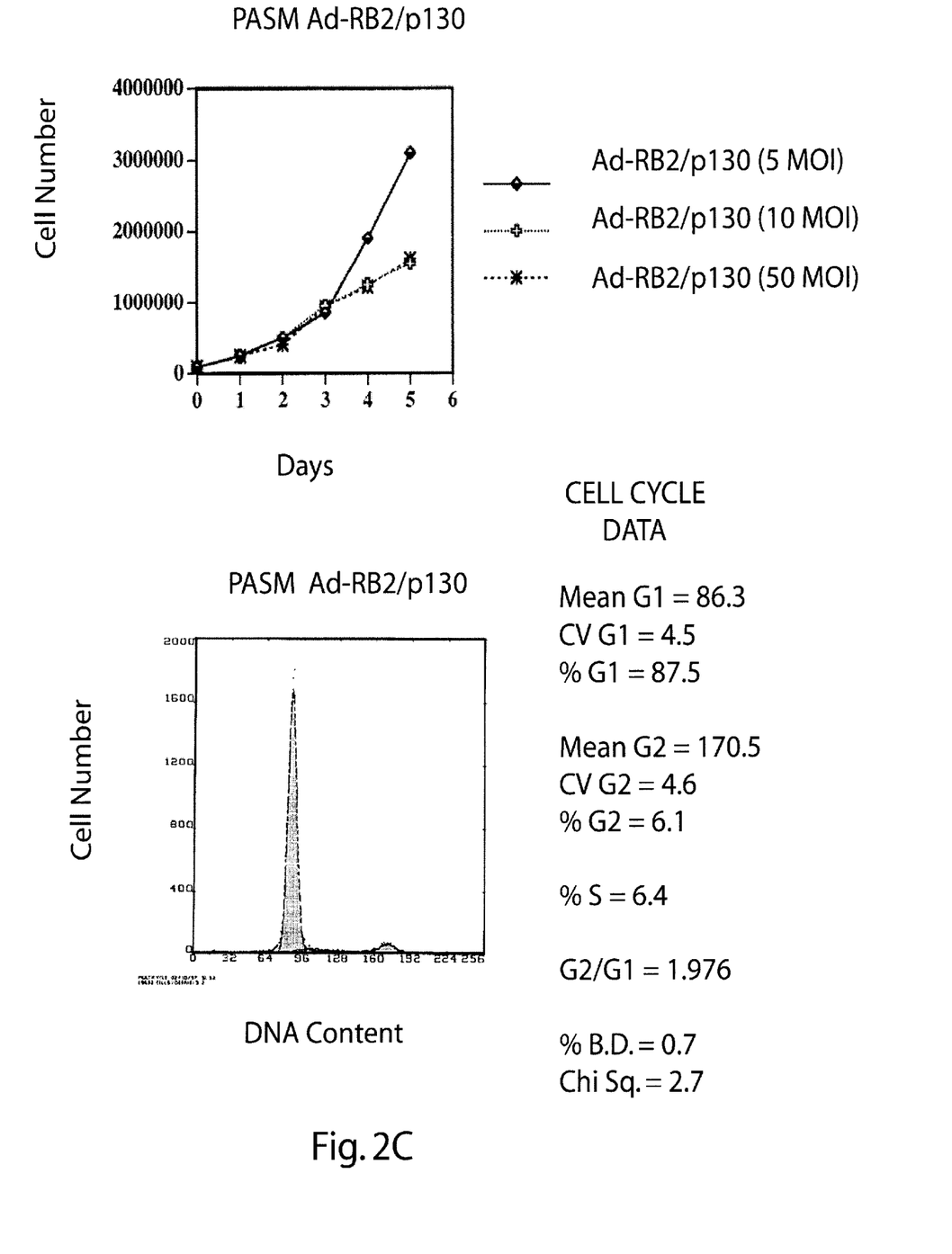

The effects of different amounts of Adenoviral particles on the growth of a pulmonary artery smooth muscle cell line (PASM) was also examined. In this experiment, PASM cells were plated at a density of $\times 10^5$ in 10 cm diameter dishes in triplicates and transduced with 5, 10 or 50 pfu/cell of either Ad-CMV, Ad-CMV-β-Gal or Ad-CMV-Rb2/130. The cells were counted by trypan blue exclusion method each day over 5 days to monitor their growth rate. In PASM cells transduced with 10 or 50 MOI of Ad-CMV-Rb2/p130 the growth rate was inhibited by almost 4 fold as compared to that of Ad-CMV and Ad-CMV-β-Gal transduced cells. Cell count in Ad-CMV infected PASM cells was found comparable to that of Ad-CMV-β-Gal infected cells. To test whether exposure of the cultured cells to Adenovirus at 50 MOI could be associated to toxicity PASM cells wee transduced with 50 MOI of either Ad-CMV, Ad-CMV-β-Gal or Ad-CMV-RB2/p130 and 48 hours later processed the samples for Facs analysis. It was observed that exposure of PASM cells to any of the three adenoviruses did not cause apparent cytotoxicity. Further, the overexpression of RB2/p130 resulted in a $G_{10}$ accumulation of the cells compared to the control (Ad-CMV and Ad-CMV-β-Gal) transduced cells.

Figure 3:
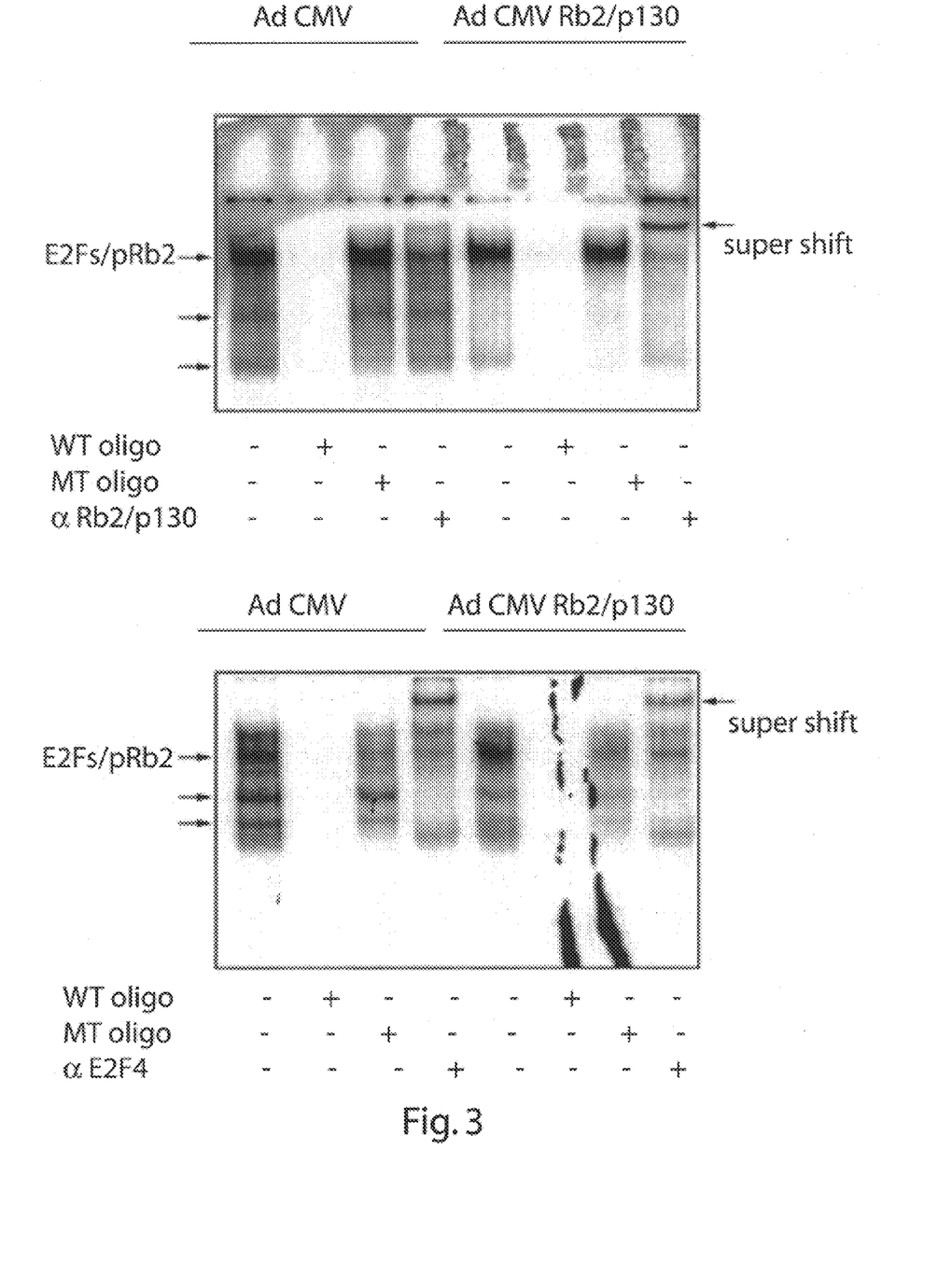
FIGS. 3a–3b show the effects of pRb2/p130 induction on E2F-binding capacity.

RB2/p130 was also demonstrated to associate in vivo with E2F family members and to inhibit their ability to transactivate genes that promote cell cycle in PASM cells. In vivo RB2/p130 associates with E2F4 and E2F5 and thereby inhibits their ability to transactivate genes that promote cell cycle progression (Sardet et al. Proc. Natl. Acad. Sci. USA 92: 2403–2407 (1995)). Since the growth suppressive function of the retinoblastoma family of proteins is thought to occur at least in part by their binding and negative regulation of specific members of the E2F family of transcription factors, the E2F complexes in PASM cells infected with either Ad-CMV-Rb2/p130 or Ad-CMV cells were analyzed. In these experiments, PASM cells were plated at a density of $2 \times 10^6$ cells and transduced with either the adenoviruses Ad-CMV or Ad-CMV-RB2/p130 at a concentration of 50 pfu/cell and harvested after 48 hours. By electrophoretic mobility shift assay (EMSA) using a oligonucleotide probe of the E2F DNA binding sequence labeled with [$^{32}$P]-γ dCTP, an E2F complex was detected that effectively competed with cold wild-type oligonucleotide but not with a point mutated oligonucleotide that abrogates E2F binding to DNA. The band of the E2F complex was supershifted by incubation with an antibody that specifically recognizes RB2/p130 as well as by an antibody that specifically recognizes E2F4 in both the Ad-CMV-RB2/p130 and Ad-CMV transduced cells. Almost the entire E2F complex was shifted in the Ad-CMV-RB2/p130 infected cells by incubation with the RB2/p130 antibody, indicating that most of the E2F is bound by RB2/p130 in these cells. However in the Ad-CMV transduced cells only a small fraction of the E2F complex was supershifted by the RB2/p130 antibody, a reflection of the low endogenous expression level of RB2/p130 in the proliferating PASM cells. This indicates that transduction of smooth muscle cells by Ad-CMV-RB2/p130 and the resulting high level of expression of RB2/p130 provides an abundance of RB2/p130 that can effectively sequester E2F activity thereby leading to growth arrest. Additionally, the band of the E2F complex, was supershifted by incubation with an antibody that recognize E2F4.

Figure 6:
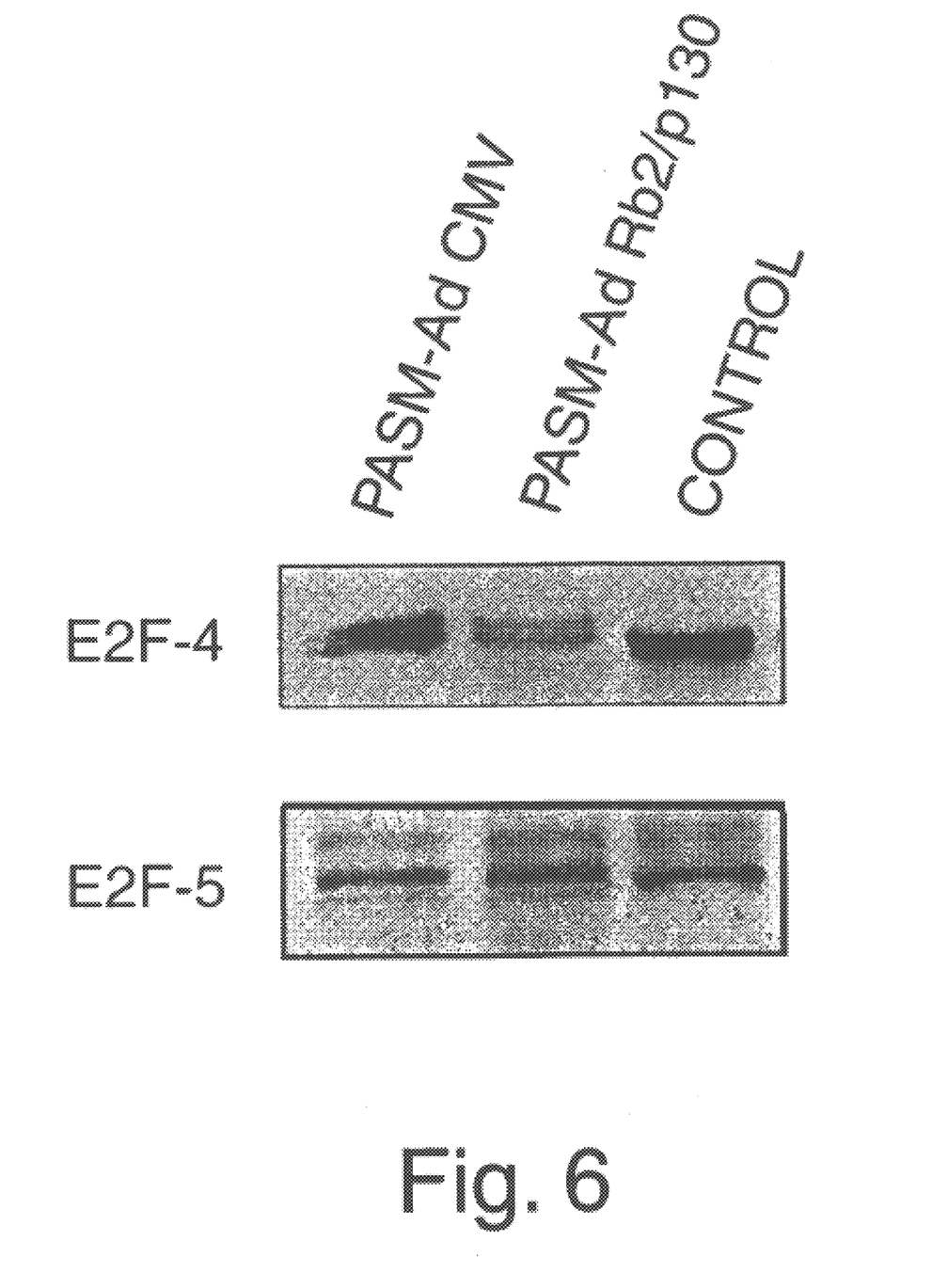
FIG. 6 is the Western blot analysis of E2F-4 and 5 in PASM cells transduced with either Ad-CMV or Ad-RB2/p130.
Figure 7:
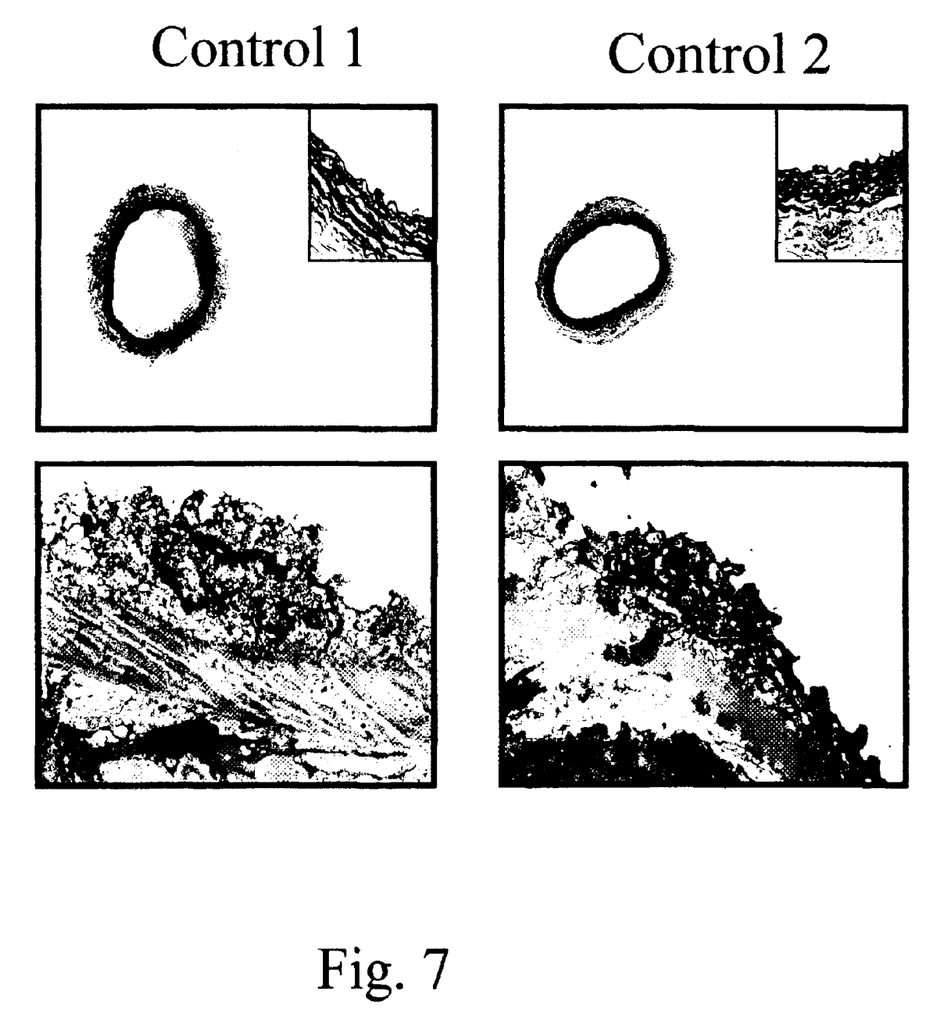
FIG. 7 shows structural and ultrastructural analysis of control vessels.

Expression of the E2F family members following transduction was also examined. It was found that the expression level of E2F5 was not effected by either adenovirus carrying RB2/p130 or adenovirus control. The expression of E2F4 was instead down-regulated upon overexpression of RB2/p130, indicating that its overexpression in PASM cells targeted E2F4 for protein instability and degradation or inhibited its transcription.

The vast majority of endogenous E2F activity during the $G_0/G_1$ transition stems from E2F4 (Cobrinik et al. *Genes & Development*. 7, 2392–2404 (1993)). In fact, during the $G_1$ phase of the cell cycle, E2F4 accounts for almost all of the free activity. During S phase an equal mixture of E2F4 and E2F1 comprises the free E2F activity (Moberg et al. *Mol. & Cell. Biol.* 16, 1436–1449 (1996)). The main form of E2F detected in the $G_0$–$G_1$ phases in primary mouse fibroblasts is E2F4 bound to RB2/p130 which is then replaced by p107E2F4 complexes in late $G_1$ (Cobrinik et al. *Genes & Development*. 7, 2392–2404 (1993); Moberg et al. *Mol. & Cell. Biol.* 16, 1436–1449 (1996)). Thus, RB2/p130 is a primary negative modulator of E2F activity in quiescent or resting cells and offers the potential for inhibiting cellular proliferation and intimal thickening after balloon angioplasty.

Figure 4:
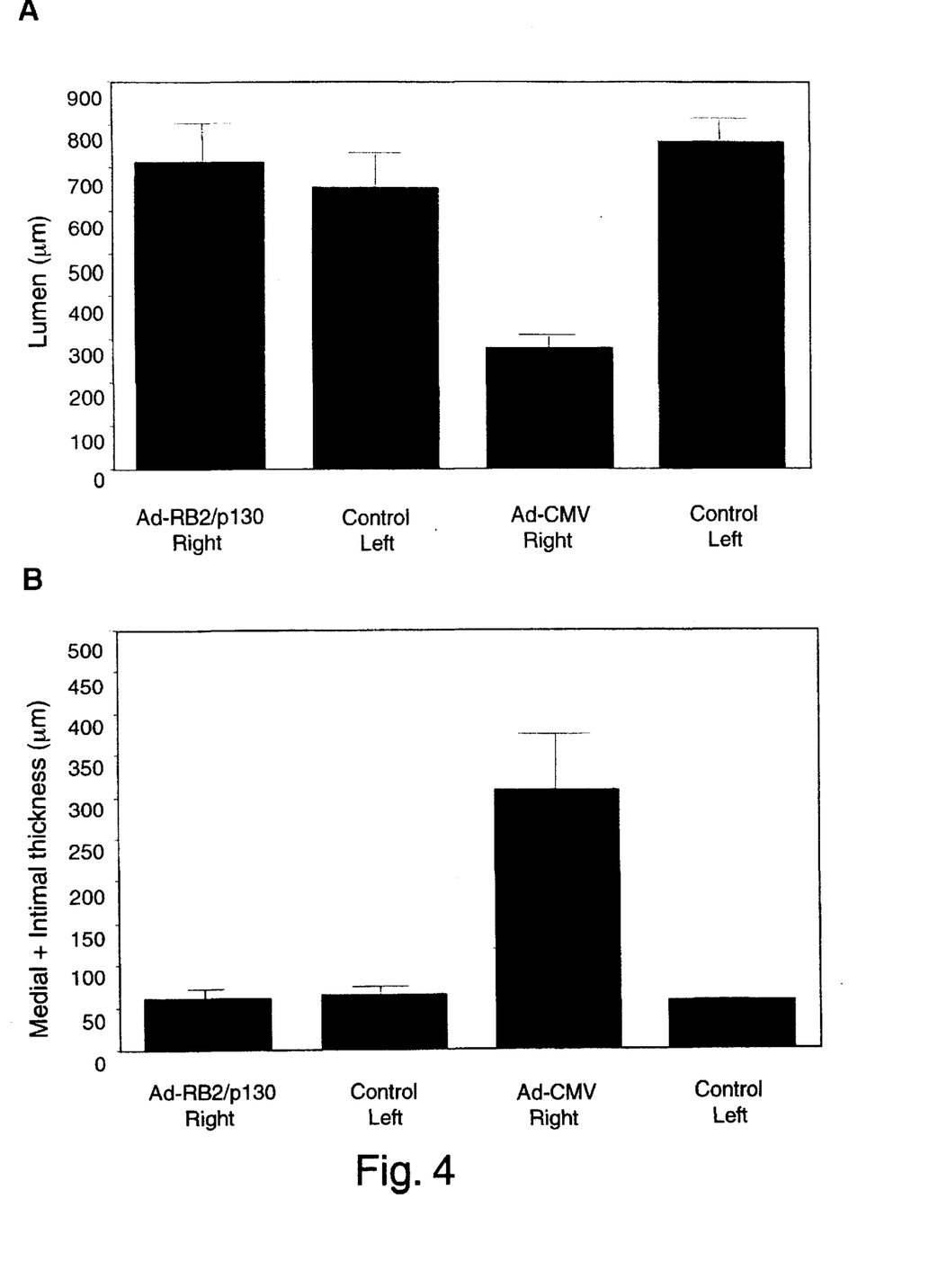
FIGS. 4a–4b is the graphic representation of lumen size (A) and arterial wall thickness (B) post angioplasty in Ad-CMV, Ad-RB2/p130 transduced carotid arteries and left carotid arteries (control).
Figure 5:
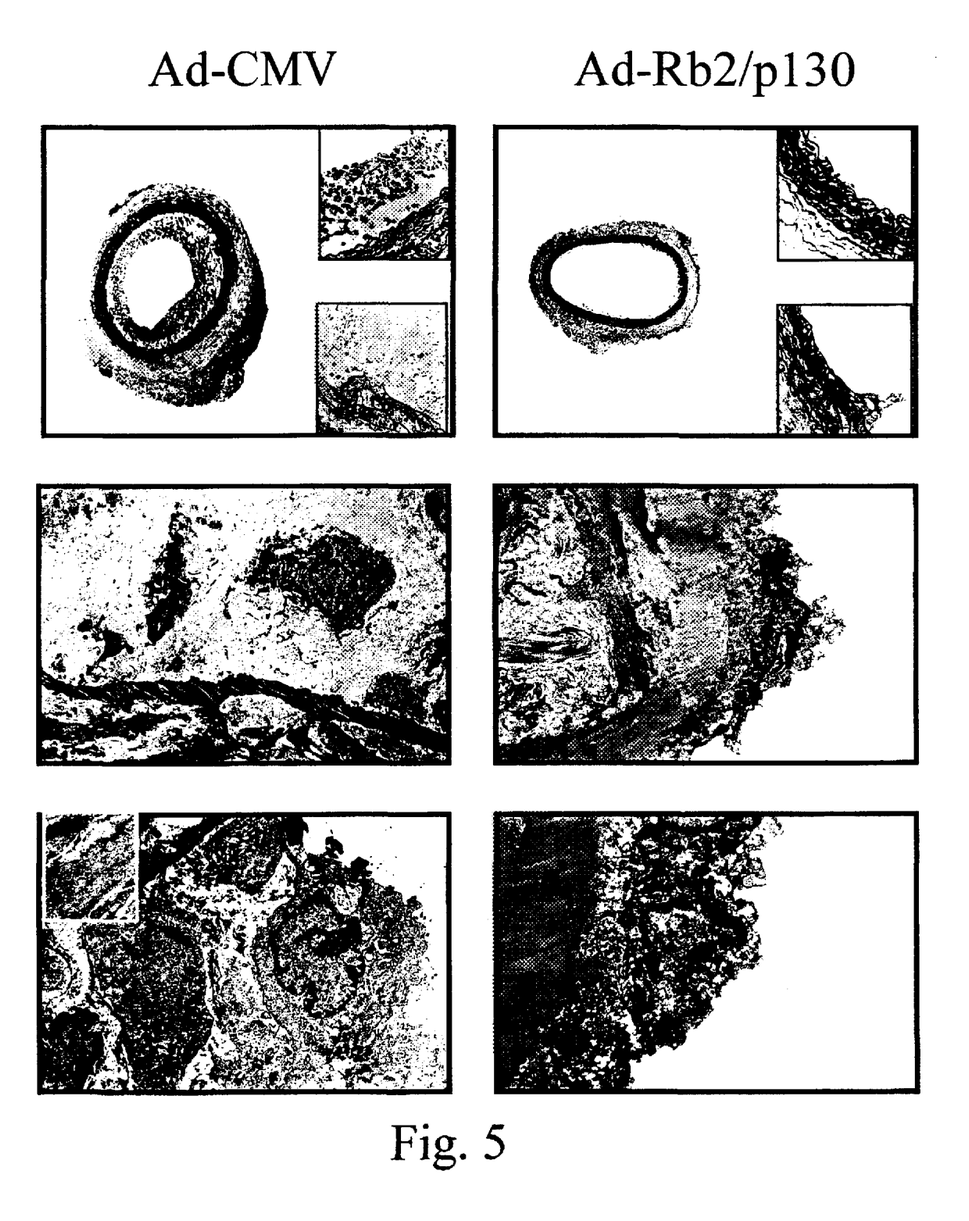
FIG. 5 shows structural and ultrastructural analysis of CMV and Rb2 vessels.

The effects of RB2/p130 transduction on neointimal formation two weeks after balloon injury were analyzed in vivo in a rat carotid artery model of restenosis (Indolfi et al. *Nature Med.* 3, 775–779 (1997); Indolfi et al. *Nature Med.* 1, 541–545 (1995)). in the animal group infused with Ad-CMV, a reproducible neointimal formation as shown by semithin sections stained with methylene blue was observed. An increase of the intimal thickness for the presence of several layers of smooth muscle cells with the interruption of the inner elastic lamina was found. This resulted in a great decrease of the lumen (Lu) (276.4 μm±25.4), and conversely an increase in the thickness of the medial and intimal carotid layer (Th) (308 μm±74) compared to the left carotid artery (Lu=758.8 μm±41.85, Th=57.4 μm±1.2) By electron microscopy the neointima of the rats treated with Ad-CMV appeared almost entirely constituted of layers of smooth muscle cells immersed into an intercellular matrix that included reticular fibrils, without any trace of neovascularization.

In the group treated with Ad-RB2/p130 neointimal formation was highly suppressed 14 days after injury. The lumen of the right carotid arteries perfused with Ad-RB2/p130 (Lu=712.38 μm±117.36) was comparable to the left uninjured side (Lu=652.63 μm±87.23). There were essentially no differences between the thickness of the arterial walls treated with Ad-RB2/p130 (Th=60.5 μm±6.18) and the normal uninjured left side (Th=64.8 μm±8.68). The differences between the animal group treated with either Ad-CMV or Ad-RB2/p130 were found to be statistically significant (P<.01). However, no statistically significant differences in the lumen size or in the arterial thickness were found between the right carotid artery treated with Ad-RB2/p130 or the left untreated carotid artery indicating that RB2/p130 greatly inhibited the proliferative capacity of the smooth muscle cells in vivo as in vitro. By electron microscopy it was demonstrated that the intimal layer of the carotid arteries treated with Ad-RB2/p130 consisted solely of endothelial cells. The morphological aspects of the Ad-RB2/p130 treated carotid arteries were compared with the contralateral uninjured side. Cross semithin sections of the left carotid arteries (controls) stained with methylene blue and observed by light microscopy showed a normal thickness of the arterial wall as well as typical endothelial cells limiting the lumen as determined by electron microscopy identical to the Ad-RB2/p130 treated carotid arteries.

Figure 8:
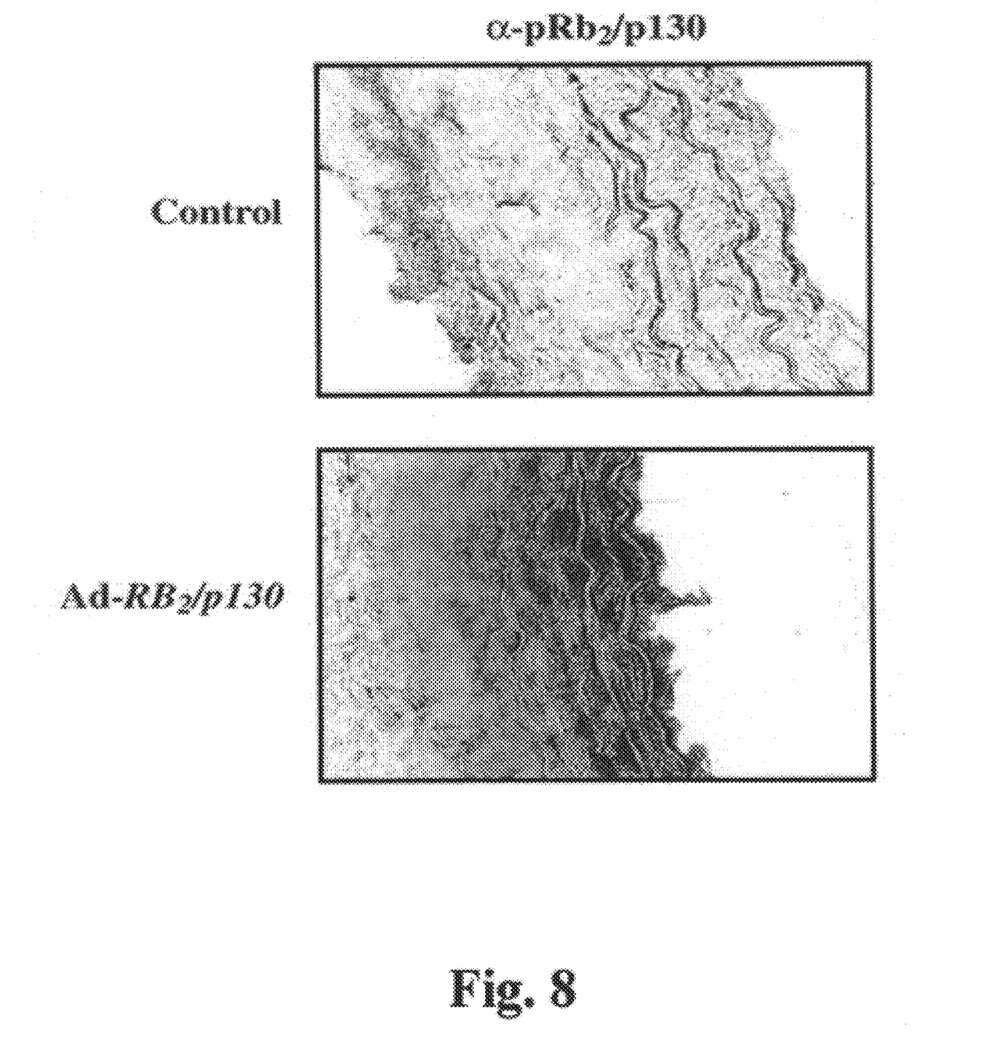
FIG. 8 shows immunohistochemical analysis of pRb2/p130 and β-galactosidase in uninjured, Ad-RB2/p130 and β-galactosidase transduced carotid arteries.

The expression levels of RB2/p130 post transduction in vivo were also examined via imnmunohistochemistry. Sections of carotid arteries treated with Ad-RB2/p130 showed a high level of RB2/p130 when compared to the left normal uninjured side, demonstrating in vivo adenoviral gene transfer of RB2/p130 and the constitutively high expression of the transduced gene after 2 weeks. The efficacy of gene transfer was determined by identifying single cells positive for nuclear pRb2/p130 staining as well as by the high expression level of β-Galactosidase transgene in Ad β-Gal infected vessels.

Accordingly, the present invention provides methods for inhibiting vascular SMC proliferation and for preventing restenosis in patient with a viral vector comprising RB2/p130. In a preferred embodiment, RB2/p130 cDNA is subcloned into an adenoviral vector in accordance with methods of plasmid construction well known in the art. As will be obvious to those of skill in the art upon this disclosure, however, appropriate vectors other than those described herein. For example, in one embodiment, a transient three-plasmid expression system (plasmids encoding env, gag-pol, and RB2/p130) can be prepared. This embodiment would involve using a retroviral vector wherein the full length cDNA sequence of RB2/p130 is subcloned into the vector. Selection of an appropriate vector is based upon adequate expression of the gene with minimal viral gene expression.

The viral vector encoding RB2/p130 is then transduced into vascular smooth muscle cells by contacting the cells with the vector. This can be accomplished using methods known to those of skill in the art. In a preferred embodiment, the viral vectors are administered to a mammal, preferably a human. In one embodiment, the vector containing the RB2/p130 gene is administered to suppress vascular smooth cell proliferation and prevent restenosis through expression of this cell proliferation suppressor gene. In this embodiment, the method of transduction will preferably be performed by intra-arterial injection to arteries. To prevent restenosis following angioplasty, it is preferred that the viral vector expressing RB2/p130 be administered to the patient at the time of the procedure.

It is preferred that the viral vectors be administered in a pharmaceutically acceptable carrier for injection such as a sterile aqueous solution or dispersion. Dose and duration of treatment is determined individually depending on the degree and rate of improvement. Such determinations are performed routinely by those of skill in the art.

The following nonlimiting examples are provided to further illustrate the present invention.

EXAMPLES

Example 1

Plasmids

The full length ORF of the RB2/p130 gene has been subcloned into the pAd-CMVlink-1vector by releasing the RB2/p130 gene from the pCDNA3-RB2/p130 construct with a HindIII-Sal I digestion and inserting it into the pAd-CMVLink-1 digested with HindIII (Claudio et al. *Cancer Research* 54, 5556–5560 (1994); Davis, A. R. and Wilson, J. M. Adenovirus Vectors. Dracopoli et al. Eds. In *Current Protocols in Human Genetics* 2, Unit 12.4 (1996)). The construct pAd-CMVLink-1-βgal has been described previously (Davis, A. R. and Wilson, J. M. Adenovirus Vectors. Dracopoli et al. Eds. In *Current Protocols in Human Genetics* 2, Unit 12.4 (1996)). The vector pAd-CMVLink-1 contains the Adenovirus 5 sequence encoding map units 0–1, a cytomegalovirus immediate early enhancer/promoter element, SV40 splice donor/acceptor site intron, SV40 polyadenylation signal, Adenovirus 5 sequence encoding map units 9–16, a synthetic multiple cloning site, and sequences from the pAT153 plasmid.

Example 2

Cell Lines 293 cells (primary embryonal human kidney cells) and PASM (Pulmonary Artery Smooth Muscle) cells were maintained in D-MEM containing 10% Fetal Bovine Serum (FBS) and L-Glutamine.

Example 3

Adenoviral Production and Transduction

The Ad-CMV-RB2/p130, Ad-CMV and Ad-CMV-βgal were generated as follows. Recombinant adenoviruses were constructed by cotransfecting the adenoviral shuttle plasmid (pAd-CMVlink-1 with the insertion of either the RB2/p130 or the Lac-Z gene behind the CMV promoter) and Cla I digested Ad5 DNA ("viral backbone") containing a GFP selection marker, into 293 primary embryonal human kidney cells. The 293 cells serve as a packaging cell line that supplies the E1 function in trans. Homologous recombination occurs in the region of overlap, in region E1 between the restricted Ad5 viral DNA ("viral backbone") and the shuttle plasmid (pAdCMVLink-1-RB2/p130). After transfection, 293 cells were overlaid with agar-containing medium and after approximately 10 days visible plaques were examined using an inverted fluorescent microscope. Non-fluorescent or "white" plaques were easily distinguished from background or "green" plaques. The white plaques were expanded by infection of 293 cells and after appearance of complete cytopathic effect, DNA was prepared by a modification of the method of Hirt (Arad, U. *Biotechniques* 24, 761–762 (1998)). DNA recombinant adenoviruses were controlled by restriction enzyme analysis. Recombinant adenoviruses were then screened by western blot analysis for expression levels of RB2/p130 using an antibody that specifically recognizes RB2/p130 Baldi et al. *J. Cell. Biochem.* 59, 402408 (1995)). The recombinant adenovirus that showed the highest expression of RB2/p130 was plaque purified once more and expanded by infection of 293 cells. Purification of the adenoviruses in the supernatant was performed by sequential equilibrium density gradients using CsCl (Davis, A. R. and Wilson, J. M. Adenovirus Vectors. Dracopoli et al. Eds. In *Current Protocols in Human Genetics* 2, Unit 12.4 (1996)). Purified viruses were stored in a solution containing 10% glycerol at −80° C. Optical density was measured and viral stocks were made at $5\times10^{12}$ particles/ml. A viral titer of $22\times10^9$ pfu/ml was determined by plaque assay for the Ad-CMV and Ad-CMV-RB2/p130 viruses. A viral titer of $40\times10^9$ pfu/ml was determined for the Ad-β-gal virus. Infection of non-permissive cells (cells lacking E1 function) confirmed that the viruses were only able to undergo one round of infection; therefore, they are replication defective.

Example 4

Determination of Growth Rates and Western Blot

PASM cells were plated at a density of $1\times10^5$/dish into 10 cm culture dishes in triplicate. Cells were transduced with $4.4\times10^7$ pfu of either Ad-CMV or Ad-CMV-RB2/p130 in DMEM medium containing 2% Fetal Bovine Serum (FBS). The next morning the medium was removed and replaced with DMEM containing 10% FBS. The cells were harvested every 24-hours for 6 days and counted by trypan blue exclusion. Cells were also spun down and pellets were lysed. Western blot analysis was performed essentially as previously described (Claudio, et al. *Cancer Res.* 56, 2003–2008 (1996)). The anti-RB2/p130 was used at a dilution of 1:1000, the anti-β-tubulin (Sigma, St. Louis, Mo.) was used at a dilution of 1:1000, and the E2F4 and 5 antibodies (Santa Cruz, Calif.) were used at a dilution of 1:500.

Example 5

Dose-response Growth Curve and Facs Analysis

PASM cells were plated at a density of $1\times10^5$/dish into 10 cm culture dishes in triplicate. Cells were transduced with 5, 10 or 50 MOI of either Ad-CMV, Ad-CMV-βGal or Ad-CMV-Rb2/p130 in DMEM medium containing 2% Fetal Bovine Serum (FBS). The next morning the medium was removed and replaced with DMEM containing 10% FBS. The cells were harvested every 24 hours for 5 days and counted by trypan blue exclusion for dose-response growth curve. For Facs analysis purpose cells were collected 48 hours after transduction and fixed in 70% ethanol and treated with a solution containing propidium iodide and RNAse A as previously described by Claudio et al., *Cancer Research* 56:2003–2008 (1996).

Example 6

Gel Shift Assay (EMSA)

PASM cells were seeded at a density of $1\times10^6$/dish into 10 cm culture dishes in duplicate. Cells were transduced with $1\times10^8$, pfu of either Ad-CMV or Ad-CMV-RB2/p130 in DMEM medium containing 2% FBS. The next morning the medium was removed and replaced with DMEM containing 10% FBS. Cells were collected and gel shift assays were performed essentially as previously described by Pagano et al. *Science* 255, 1144–1147 (1992).

Example 7

Animal Studies

All WKY rats were maintained under identical conditions of temperature (21±1° C.), humidity (60±5%) and light/dark cycle, and had free access to normal rat diet. The animal group treated with either Ad-CMV or Ad-RB2/p130 consisted of 10 rats each, while the group infused with Ad-β-Gal consisted of 5 rats.

The right common artery of 35 WKY rats at 14 weeks of age (Charles River, Morini, Italy) weighing 350 to 400 g was denuded of endothelium by the intraluminal passage of a balloon embolectomy catheter (2F' Fogarty, Edwards Laboratories) introduced through the external carotid artery. All animals were anesthetized with an intraperitoneal injection of ketamine (Ketalar, Parke-Davis) 80 mg/kg and xilazine (Rompun, Bayer AG) 5 mg/kg. The right common and external carotid artery was surgically exposed and an arteriotomy was performed in the external carotid artery. Deendothelializing injury of a right common artery segment was achieved by insertion and passage of a 2F Fogarty balloon catheter, distended sufficiently with saline solution to generate slight resistance by an inflation at 1.5 atm with a calibrated device (Indeflator Plus 20, Advanced Cardiovascular System, Inc.). To ensure adequate endothelial damage, the inflated catheter was passed a total of three times. This technique produced distension of the carotid itself. The time of balloon inflation was kept constant for twenty seconds. After balloon injury a segment of common artery approximately one cm in length was isolated placing vascular clamps on the proximal common artery and proximal internal artery. A polyethylene catheter (PE 50, Hecton Dickinson) was introduced through the external carotid arteriotomy and the isolated vessel segment was flushed with M-199 medium before introduction of either adenoviral vectors. Adenoviral vectors were defrosted, diluted ($1 \times 10^9$ pfu/μL) and kept in wet ice until use. All stocks were used within two hours of thawing. For each rat a total of 50 μL diluted adenoviral vector were instilled into the isolated common carotid segment by means of a catheter placed in the external carotid artery. During infusion of the vector-containing medium, the isolated carotid segment became distended and remained so for the duration of the instillation period. After twenty minutes of incubation, the vector-containing medium was withdrawn, the external carotid artery was ligated and the blood flow through the common and internal carotid arteries was reestablished. Rats were allowed to recover from anesthesia and were returned to their cages.

Example 8

Morphology

Two weeks after gene transduction, carotid arteries were dissected free from the surrounding tissues and rats were sacrificed.

Structural and ultrastructural analysis of blood vessel wall and lumen were performed on specimens fixed in universal solution (4% paraformaldehyde and 1% glutaraldehyde in 0.1 M phosphate buffer). The delay to fixation was approximately 2–3 hours. Blood vessels were washed twice in PBS and postfixed in 1% osmium tetroxide. Then the specimens were rinsed two times in PBS, followed by dehydration through a series of alcohols (30% to 100%, 15 min steps). The embedding was performed in epoxy resin (Epon 812) and polymerized at 60° C. overnight. Semithin cross sections (0.5 μm), were cut in a Ultracut-E (Reichert-Young), mounted onto slides and stained by warm methylene blue. Screening and photography were performed using a Zeiss microscopy.

Ultrathin cross sections (60 nm) were mounted on copper grids, counterstained with uranyl acetate for 6 minutes and lead citrate for 5 minutes. The specimens were analyzed by a JEOL JEM-1220 electron microscope.

Blood vessel wall thickness and lumen diameter were evaluated using a Digital Imaging Processing (Image-Pro Plus, Media Cybernetics, Silver Spring Md., USA). For immunohistochemical purposes, serial frozen blood vessel sections (5 μm) were allowed to equilibrate to room temperature for 12 hours and exposed to acetone for 10 minutes. A biotin-streptavidin (Vectastain Universal Quick Kit, Vector Laboratories, Inc., Burlingame, Calif.) preformed complex was used to detect the expression of RB2/p130. Sections were preblocked with 10% horse serum/PBS+0.2% Tween-20 for 20 minutes at room temperature. Tissue sections were eliminated of excess serum and incubated with our specific polyclonal anti-pRb2/p130 or horse serum at appropriate dilutions (De Luca et al. *Mature Med.* 3, 913–916 (1997)). After washing, bound primary antibodies were detected by a universal biotinylated antibody prediluted in TBS at room temperature for 20 minutes followed by incubation for 10 minutes with a peroxidase-conjugated streptavidin. 3-amino-9ethylcarbazole (AEC) was used as the calorimetric substrate. Analysis of blood vessel sections was performed by a Zeiss light microscopy.

Example 9

Statistical Analysis

All data shown are means ± s.e.m. Statistical analysis between groups was performed by analysis of variance (ANOVA) using a Systat program (Systat INC, Evanston, Ill.). Tukey's test was applied to compare single mean values when a significant overall effect was determined. Dixon, W. J. et al., *Introduction to Statistical Analysis*, New York, McGraw-Hill (1969). A P value of <.05 was considered statistically significant All publications and references, including but not limited to patent applications, cited in this specification, are herein incorporated by reference in their entirety as if each individual publication or reference were specifically and individually indicated to be incorporated by reference herein as being fully set forth.

While this invention has been described with a reference to specific embodiments, it will be obvious to those of ordinary skill in the art that variations in these methods and compositions may be used and that it is intended that the invention may be practiced otherwise than as specifically described herein. Accordingly, this invention includes all modifications encompassed within the spirit and scope of the invention as defined by the claims.

What is claimed is:

1. A method of inhibiting vascular smooth muscle cell proliferation comprising transducing vascular smooth muscle cells by intraarterial local instillation of an adenoviral vector expressing RB2/p130.

2. A method of preventing restenosis in a patient which comprises administering to a patient by intraarterial local installation of an adenoviral vector expressing RB2/p130.

\* \* \* \* \*